United States Patent
Hommann et al.

(10) Patent No.: US 7,357,790 B2
(45) Date of Patent: Apr. 15, 2008

(54) AUTO-INJECTOR WITH ACTIVE AGENT CONTAINER LATCHING

(75) Inventors: Edgar Hommann, Grossaffoltern (CH); Benjamin Scherer, Uster (CH)

(73) Assignee: TecPharma Licensing AG, Burgdorf (CH)

( * ) Notice: Subject to any disclaimer, the term of this patent is extended or adjusted under 35 U.S.C. 154(b) by 264 days.

(21) Appl. No.: 11/016,539

(22) Filed: Dec. 17, 2004

(65) Prior Publication Data

US 2005/0203466 A1    Sep. 15, 2005

(30) Foreign Application Priority Data

Dec. 18, 2003  (CH) .................................. 2186/03

(51) Int. Cl.
*A61M 5/32* (2006.01)

(52) U.S. Cl. ........................................ 604/198

(58) Field of Classification Search .......... 604/110, 604/195–198, 192, 232–235
See application file for complete search history.

(56) References Cited

U.S. PATENT DOCUMENTS

| 4,487,602 | A |   | 12/1984 | Christensen et al. |         |
|-----------|---|---|---------|--------------------|---------|
| 4,801,295 | A | * | 1/1989  | Spencer            | 604/198 |
| 5,609,577 | A | * | 3/1997  | Haber et al.       | 604/110 |
| 5,681,291 | A |   | 10/1997 | Galli              |         |
| 6,280,421 | B1 | * | 8/2001 | Kirchhofer et al. | 604/218 |
| 6,575,939 | B1 |   | 6/2003 | Brunel             |         |
| 6,767,336 | B1 | * | 7/2004 | Kaplan             | 604/136 |
| 2003/0036725 | A1 |  | 2/2003 | Lavi et al.       |         |
| 2004/0225262 | A1 | * | 11/2004 | Fathallah et al. | 604/198 |

FOREIGN PATENT DOCUMENTS

| EP | 0577448 A | 1/1994 |
| EP | 0 666 084 A2 | 8/1995 |

* cited by examiner

*Primary Examiner*—Kevin C. Sirmons
*Assistant Examiner*—Elizabeth MacNeill
(74) *Attorney, Agent, or Firm*—David E. Bruhn, Esq.; Dorsey & Whitney LLP

(57) ABSTRACT

In an elongated casing, an active agent container connected to an injection needle can be shifted axially by a spring force. Auto-injectors which are sold or distributed filled and with the springs tensed have to be provided with a needle protecting cap to ensure the sterility of the injection needle. When such a needle protecting cap is removed as preparation for using the auto-injector, a tensile force can be exerted on the active agent container. Therefore, the active agent container comprising the injection needle must be prevented from being undesirably pulled forwards. At least one latching tongue prevents the active agent container from being prematurely shifted with respect to the casing, by abutting a flange arranged on a sliding sleeve which accommodates the active agent container. When the auto-injector is placed onto a person's skin, a needle protecting tube is shifted into the casing, forcing the latching tongue away from the flange and, thus, freeing the travel path for needle movement.

37 Claims, 6 Drawing Sheets

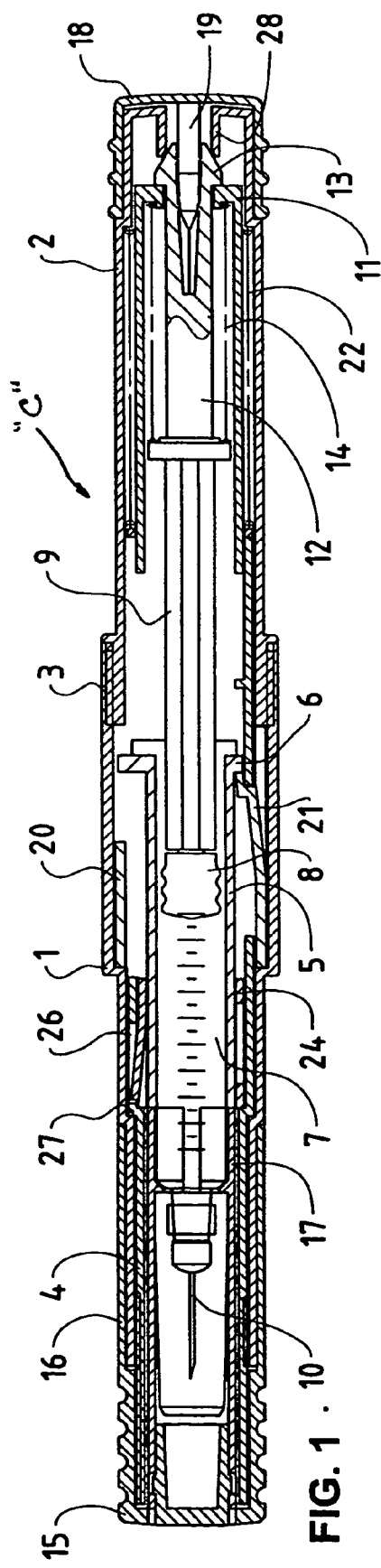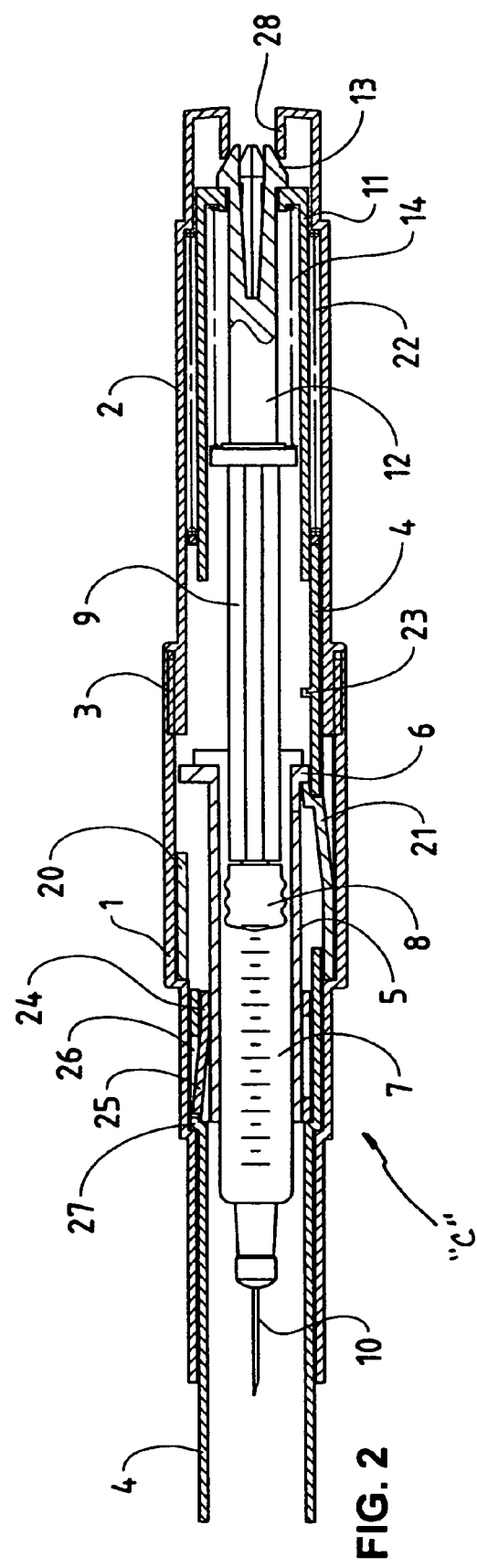
FIG. 1
FIG. 2

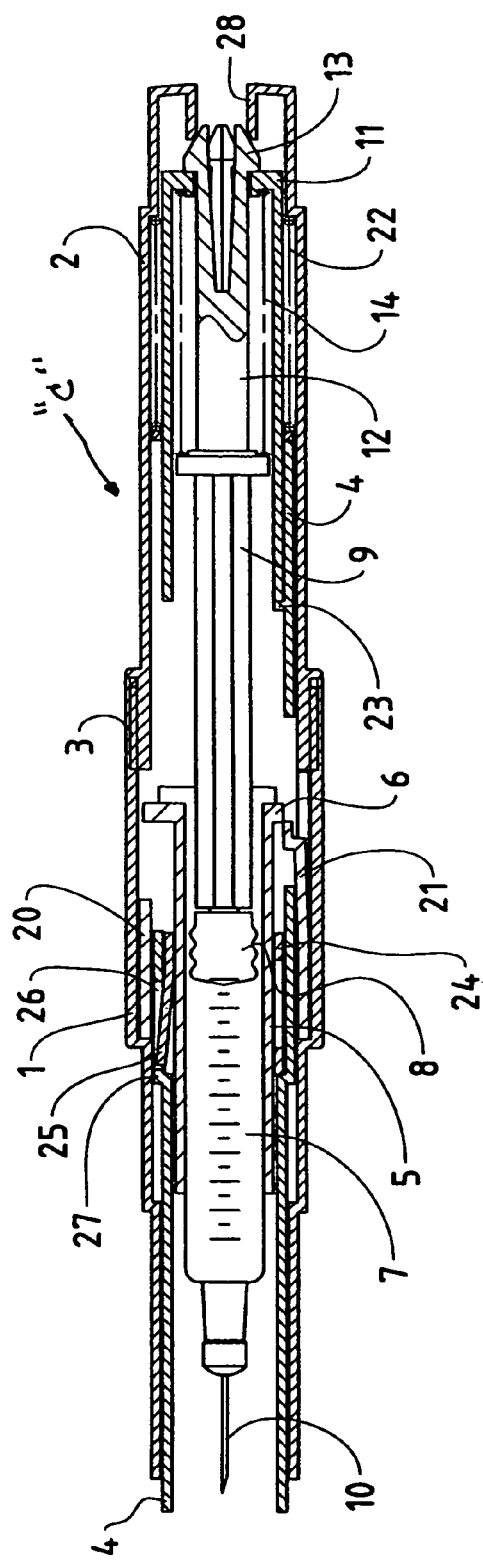
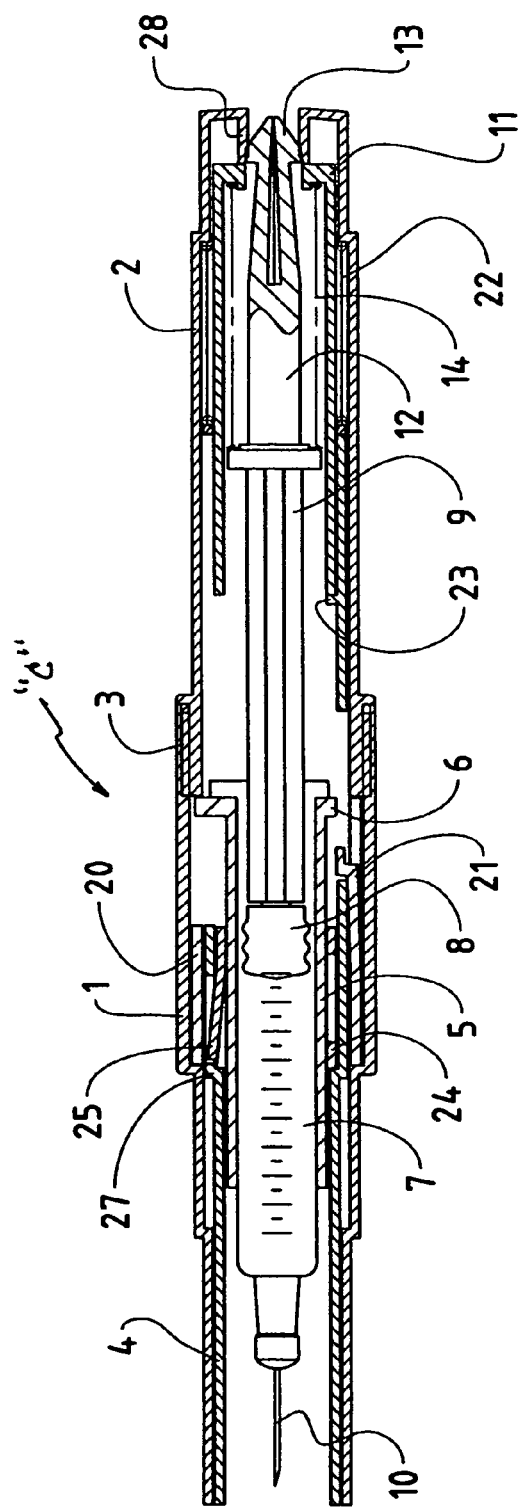
FIG. 3
FIG. 4

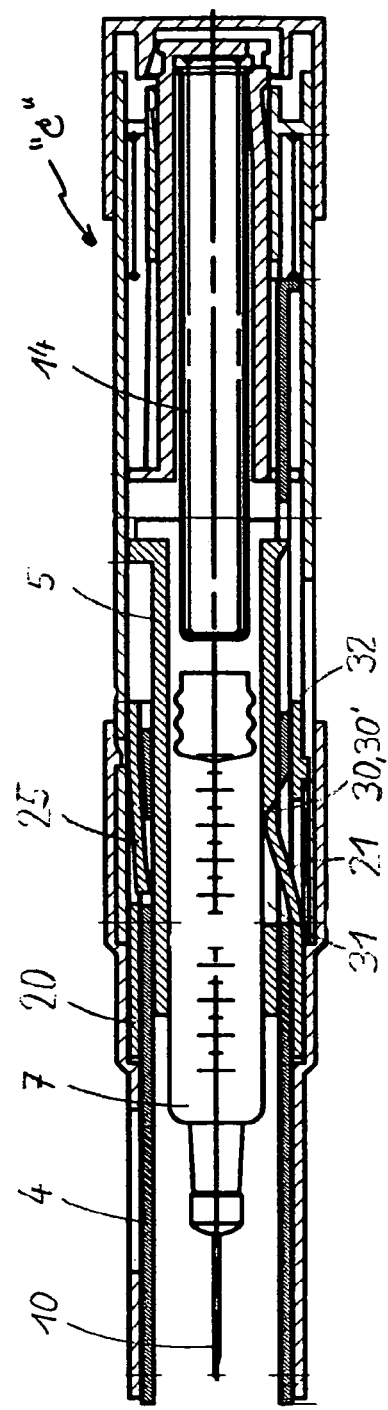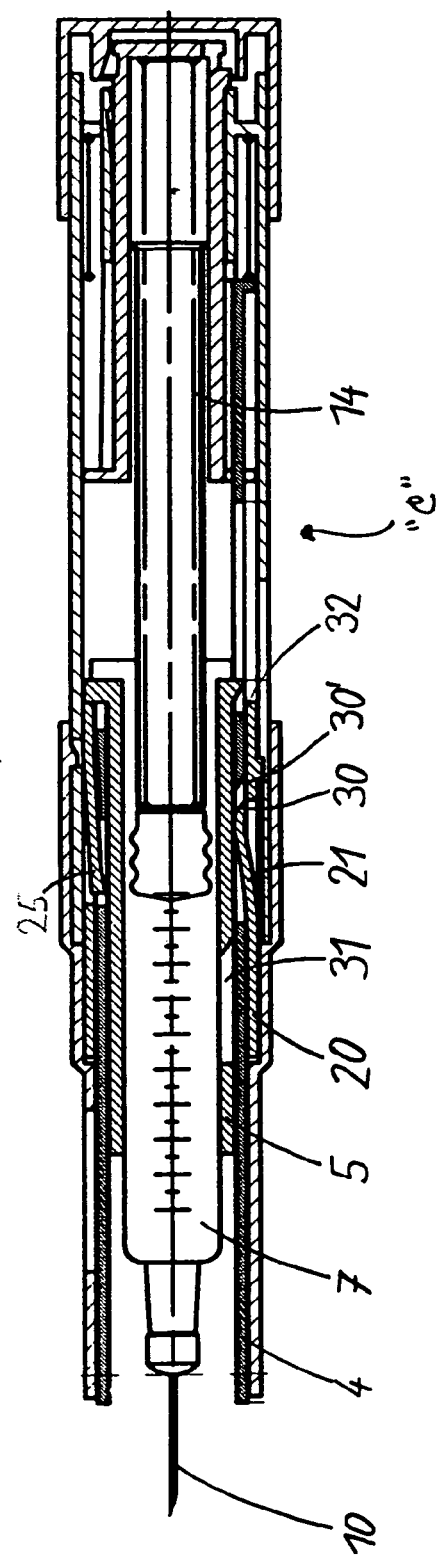

AUTO-INJECTOR WITH ACTIVE AGENT CONTAINER LATCHING

CROSS-REFERENCE TO RELATED APPLICATIONS

This application claims priority to Swiss application No. CH 2186/03, filed on Dec. 18, 2003, the content of which is incorporated by reference herein in its entirety.

BACKGROUND

The invention relates to devices and methods for the administration or delivery of substances, including the administration of medicinal substances to patients. More particularly, it relates to injection or infusion devices and methods, and to an auto-injector for automatically injecting an active agent. In one embodiment, the auto-injector comprises an elongated casing, an injection needle which can be shifted axially in the casing and is connected to an active agent container, a piston which can be shifted in the active agent container for the purpose of delivering the active agent, and a needle protecting tube which can be shifted relative to the casing.

Auto-injectors are known in many different embodiments. They serve to administer injections, in particular by a patient him or herself. When used, an injection needle is automatically inserted, in the majority of cases by means of a spring force, and then an active agent is injected. Many reusable auto-injectors are known and also those which, once used, are partially or completely thrown away. Auto-injectors which are sold or distributed filled and with the springs tensed have to be provided with a needle protecting cap in order to be able to ensure the sterility of the injection needle. Since this needle protecting cap preferably encloses the active agent container connected to the injection needle, forming a seal, a certain tensile force is necessarily exerted on the active agent container as the needle protecting cap is removed in preparation for using the auto-injector.

SUMMARY

In one embodiment, the present invention addresses the object of preventing an active agent container, comprising an injection needle, from being undesirably moved, e.g., pulled forward, for example when removing a needle protecting cap.

This object is addressed in accordance with one embodiment of the invention by providing an injection device with a latching member that, in a latching position, prevents the active agent container from being shifted with respect to the casing of the device, and by providing that the latching member can be moved to a release position, in which it allows the active agent container to be shifted with respect to the casing, by shifting a needle protecting tube into the casing. In one embodiment, the latching member is preferably fixed and/or locked in the latching position by the needle protecting tube.

In one embodiment, the present invention comprises an automatic injection device comprising an elongated casing, and an active agent container connected to an injection needle, wherein the container can be shifted axially by a spring force. Such auto-injectors which are sold or distributed filled and with the springs tensed have to be provided with a needle protecting cap to ensure the sterility of the injection needle. When such a needle protecting cap is removed as preparation for using the auto-injector, a tensile force can be exerted on the active agent container. Therefore, the active agent container comprising the injection needle should be prevented from being undesirably pulled forwards. At least one latching tongue prevents the active agent container from being prematurely shifted with respect to the casing, by abutting a flange arranged on a sliding sleeve which accommodates the active agent container. When the auto-injector is placed onto a person's skin, a needle protecting tube is shifted into the casing, forcing the latching tongue away from the flange and, thus, freeing the travel path for needle movement.

The present invention not only has the advantage that the active agent container remains in position in the auto-injector when the needle protecting cap is removed, but also that the auto-injector is prevented from being intentionally or unintentionally triggered until the needle protecting tube has been shifted into the casing.

In accordance with a preferred embodiment of the invention, the latching member is formed as at least one elastically flexible latching tongue. The tongue can be arranged on the casing itself or, in some preferred embodiments, on a latching sleeve mounted in the casing and formed integrally with the latching sleeve. These measures make it easier to manufacture the components from plastic in an injection moulding process, but alternatives exist, including forming the tongue and sleeve separately and then operably coupling them.

In one embodiment, the latching member preferably prevents the active agent container from being shifted with respect to the casing by abutting a flange arranged on a sliding sleeve which accommodates the active agent container. As it is shifted into the casing, the needle protecting tube forces the latching member away from said flange. This design is simple and operationally reliable.

In accordance with another preferred embodiment of the invention, the latching member comprises a surface which runs or extends obliquely with respect to the longitudinal axis of the auto-injector and abuts a surface, likewise running or extending obliquely with respect to the longitudinal axis of the auto-injector, on the sliding sleeve which accommodates the active agent container. In some embodiments, the oblique surfaces of the latching member and the sliding sleeve ideally run parallel to each other. In some preferred embodiments, the oblique surfaces are each arranged on facing sides of the latching member and the sliding sleeve, such that the tip of the oblique surface of the latching member is provided on a surface of a latching sleeve, the surface pointing outwards from the auto-injector.

In the latching position, the oblique surfaces abut each other and the latching member is held in this position by the needle protecting tube. When the needle protecting tube is shifted into the casing, the latch is released. As soon as pressure is exerted on the sliding sleeve, so as to advance the active agent container comprising the needle for injecting, the oblique surface of the latching member slides outwardly along the oblique surface of the sliding sleeve, such that the sliding sleeve can be advanced. The latching member is therefore moved or forced out of the latching position by the sliding sleeve.

In accordance with another embodiment of the invention, a needle protecting cap is provided which preferably fulfils a double function in that it prevents the needle protecting tube from retracting into the casing when it is placed on the auto-injector. To this end, the needle protecting cap preferably comprises an inner sleeve reaching over the active agent container and an outer sleeve reaching over the needle protecting tube.

BRIEF DESCRIPTION OF THE DRAWINGS (Each of the first seven figures depicts a longitudinal section through one embodiment of an auto-injector in accordance with the present invention, wherein a different operational state is depicted in each figure).

FIG. 1 depicts the condition on delivery;

FIG. 2 depicts the state in which the auto-injector is unlocked;

FIG. 3 depicts the state in which the auto-injector is placed on the point of injection;

FIG. 4 depicts triggering;

FIG. 9 depicts the auto-injector embodiment of FIG. 8 in a releasing position;

FIG. 10 depicts the auto-injector embodiment of FIG. 8 in a position in which the needle has been injected.

DETAILED DESCRIPTION

Figure 5:
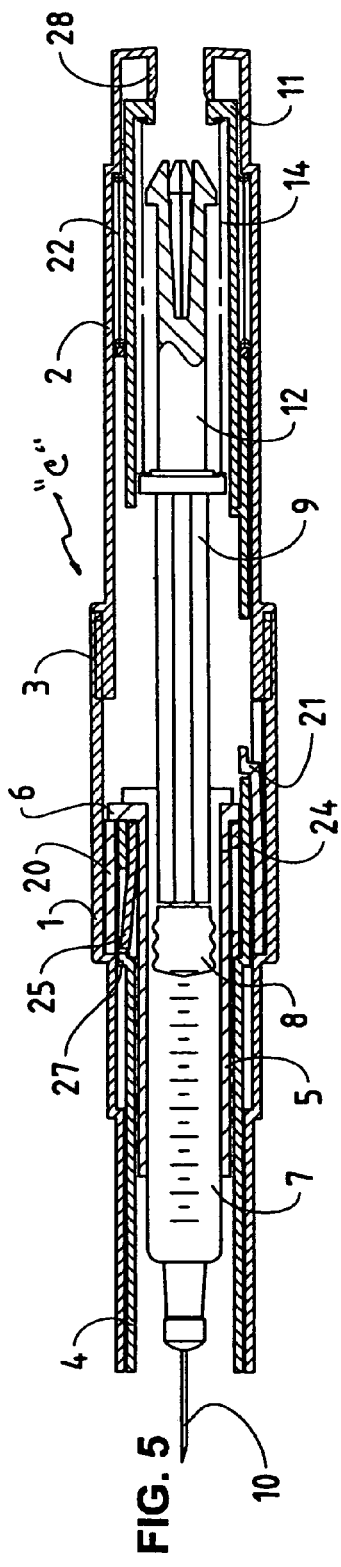
FIG. 5 depicts the end of injecting.

The drawings depicts one exemplary embodiment of an auto-injector in accordance with the present invention. The depicted auto-injector has a casing "C" comprised of a front casing part 1 and a rear casing part 2, wherein the two casing parts are joined together by a connection 3. If the auto-injector is a refillable auto-injector, the connection 3 is releasable, for example, it may comprise a threaded connection. If, however; the auto-injector is a disposable, the connection 3 can be fixed, for example, by a fused connection, adhesive connection or latching connection. On the left in the figures, a needle protecting tube 4 can be seen which can be shifted axially in the front casing part 1, as will be described in more detail below. A sliding sleeve 5 which can be shifted axially is guided in the needle protecting tube 4 via its front end and in the front casing part 1 via a flange 6 formed on its rear end. The sliding sleeve 5 accommodates an ampoule-like active agent container 7, in the interior of which a piston 8 can be shifted axially with the aid of a piston rod 9, for the purpose of delivering the active agent. At its front end, the active agent container 7 is provided with an injection needle 10.

A locking member in the form of a locking sleeve 24 is mounted externally on the sliding sleeve 5. At least one locking tongue 25 protrudes elastically outwards from the locking sleeve 24 and in the operational state in accordance with FIG. 1 abuts an inner heel 27 of the needle protecting tube 4. A cavity 26 which is formed in the needle protecting tube 4 and into which the locking tongue 25 protrudes is connected to the heel 27. The function of the locking sleeve 24 and the locking tongue 25 will be set forth further below. A guiding sleeve 11 is arranged in the rear casing part 2, such that it can be shifted axially. A driving part 12, which protrudes backwards out of the guiding sleeve 11 and abuts an end flange of the guiding sleeve 11 via latching projections 13, is situated in the guiding sleeve 1. The driving part 12 contacts the piston rod 9 and is biased against it by a driving spring 14.

In FIG. 1, the auto-injector is depicted in its latched position. This position is useful for the delivery, shipment, sale or storage of the auto-injector since it secured against being intentionally or unintentionally activated and is protected from contamination. A needle protecting cap 15 on the side of the injection needle 10 serves this purpose and has an outer sleeve 16 reaching over the front casing part 1 and the needle protecting tube 4 and an inner sleeve 17 reaching over the injection needle 10 and the front end of the active agent container 7 which encloses it, forming a seal, and thus ensures that the injection needle 10 is clean and sterile. In addition, the attached needle protecting cap 15 also secures the auto-injector against being intentionally or unintentionally triggered, by preventing the needle protecting tube 4 from being touched or shifted.

A securing cap 18, which comprises a securing pin 19 in its centre, is placed on the rear end of the auto-injector, on the right in the figures. The securing pin 19 protrudes between the latching projections 13 of the driving part and thus reliably prevents an injection from being triggered. In order to prepare the auto-injector for use, the needle protecting cap 15 and the securing cap are removed. It is clear that when the needle protecting cap 15 is removed, a tensile force is exerted on the active agent container 7 as a result of the static friction between the inner sleeve 17 and the active agent container 7. Consequently, the active agent container 7 must be prevented from leaving its position (e.g., being undesirably moved or pulled forward) in the auto-injector when the needle protecting cap 15 is removed.

For this purpose, a latching sleeve 20 is mounted in the front casing part such that it cannot move axially and at least one latching tongue 21 is arranged on the latching sleeve 20. Three latching tongues 21 are preferably provided in one embodiment, arranged or distributed symmetrically around the circumference of the latching sleeve. As FIG. 1 clearly shows, the free end of the latching tongue 21 abuts the flange 6 of the sliding sleeve 5 and thus prevents the sliding sleeve 5 from being pulled forwards together with the active agent container 7 arranged in it.

FIG. 2 shows the auto-injector after the needle protecting cap 15 and the securing cap 18 have been removed as described above. The latching member 20 is still in the latching position and the latching tongue 21 prevents the active agent container 7, comprising or carrying the injection needle 10, from being slid forward. In addition, at the then open end, the needle protecting tube 4 creates a distance which prevents the injection needle 10 from being touched or at least makes it difficult to touch the injection needle 10. The needle protecting tube 4 is held in this position by the force of a spring 22 which is clamped between the rear end of the needle protecting tube 4 and the rear casing part 2.

FIG. 3 shows the auto-injector in a position which it assumes when it is pressed onto the skin of a patient but has not yet been triggered. The needle protecting tube 4 has been shifted backwards into the casing as compared to the position of FIG. 2, compressing the spring 22, such that the tip of the injection needle 10 is then situated slightly above the skin of the patient. FIG. 3 also shows that the needle protecting tube 4 shifted backwards has forced the latching tongue 21 outwards, which then exposes the flange 6 of the sliding sleeve 5. As compared to FIG. 2, it can be seen that a flange 23 formed internally in the rear part of the needle protecting tube 4 then abuts the front facing side of the guiding sleeve 11. It should be noted that the needle protecting tube still protrudes out of the front casing part 1 by a remaining amount at the front. However, as compared to FIGS. 1 and 2, it should be clear that the needle protecting tube 4 has slid the locking sleeve 24 some distance backward on the sliding sleeve 5.

FIG. 4 shows the auto-injector at the moment of triggering. Proceeding from the state depicted in FIG. 3, the user has pressed the auto-injector slightly harder onto the skin, such that the needle protecting tube 4 has been shifted into the casing by the remaining amount mentioned above, wherein the flange 23 has shifted the guiding sleeve 11 backwards in the rear casing part 2 by the remaining amount and the latching projections 13 have been moved into the region of a triggering ring 28 arranged in the rear end of the rear casing part 2. The triggering ring 28 has contacted and/or pressed the latching projections 13, formed on elastic arms of the driving part, far enough against each other that they are then pulled through the end opening of the guiding sleeve 11 by the force of the driving spring 14. The force of the driving spring 14 then acts, unobstructed, on the piston 8 via the piston rod 9, the piston 8 in practice abruptly increasing the hydraulic pressure in the active agent container 7. This pressure slides the active agent container forwards, such that the injection needle 10 penetrates into the skin of the patient. Since the diameter of the passageway in the injection needle 10 is comparatively small, at most a very small amount of the active agent can exit the injection needle 10 in this short period of time between triggering and the injection needle 10 penetrating into the skin.

Figure 6:
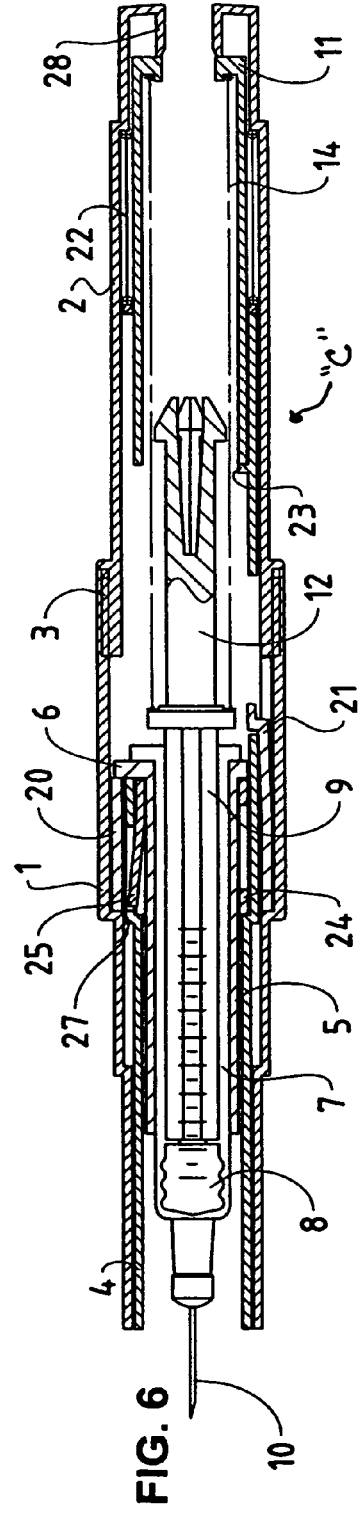
FIG. 6 depicts the end of delivering the active agent.

The injection stroke is complete when the flange 6 of the sliding sleeve 5 abuts the end of the needle protecting tube 4 and/or the end of the locking sleeve 24. FIGS. 5 and 6 show the auto-injector in the position in which the injection needle 10 is inserted or injected, wherein FIG. 5 shows the operational state at the beginning of delivering the active agent and FIG. 6 shows the state of the auto-injector after the active agent container 7 has been completely emptied. When the operational state in accordance with FIG. 6 has been reached, the user retracts the auto-injector in order to remove the injection needle 10 from his skin.

Figure 7:
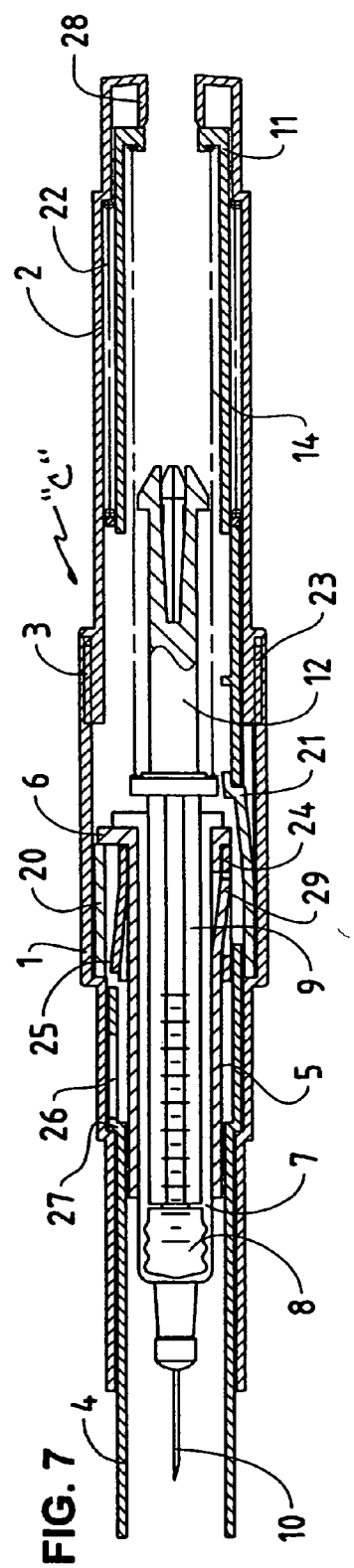
FIG. 7 depicts the state once used.

FIG. 7 shows the operational state after the injection needle 10 has been removed from the skin of the patient. The needle protecting tube 4 was shifted back into its initial state by the force of the spring 22 as soon as the auto-injector was lifted from the skin of the patient. It then mainly serves to substantially cover the injection needle and protect the user and other persons from injuries from the injection needle 10. Consequently, the needle protecting tube 4 must be prevented from being shifted relative to the injection needle 10 such that the injection needle 10 protrudes out of the needle protecting tube 4. This task is accomplished by the locking tongue 25, which is formed in the locking sleeve 24. While the needle protecting tube 4, as mentioned, has been shifted forwards by the spring force, the locking sleeve 24 maintains its position on the sliding sleeve 5 as a result of a latch tongue 29 formed on the sliding sleeve 5, which then protrudes into a cavity of the locking sleeve 24 in the position in accordance with FIG. 7 and thus fixes it in place on the sliding sleeve 5.

As can clearly be seen in FIG. 7, the free end of the locking tongue 25 at the rear end of the needle protecting tube 4 then protrudes into its path. Thus, the needle protecting tube 4 cannot be retracted without the locking sleeve 24, the sliding sleeve 5 and the active agent container 7 together with the injection needle 10, being shifted backwards relative to the front casing part 1 and the rear casing part 2, against the force of the driving spring 14. Thus, the injection needle 10 maintains its relative position with respect to the needle protecting tube 4 and the injection needle 10 is reliably prevented from being intentionally or unintentionally touched. This solution has the advantage that the axially directed force to be absorbed by the locking tongue 25 never exceeds the force of the driving spring 14, irrespective of how hard one presses against the front end of the needle protecting tube 4.

FIGS. 8 to 11 show another embodiment of an auto-injector in accordance with the present invention. In these figures, identical elements and elements having substantially the same function are denoted using the reference numerals from FIGS. 1 to 7. In this embodiment, the latching tongue 21 is guided by means of surfaces on the latching tongue 21 and the sliding sleeve 5, the surfaces running or extending obliquely with respect to the longitudinal axis of the auto-injector. The latching tongue 21 for latching the active agent container or the sliding sleeve 5 and the locking tongue 25 for latching the needle protecting tube 4 are also both arranged on the latching sleeve 20. In some preferred embodiments, the latching tongue 21 and the locking tongue 25 are formed integrally with the latching sleeve 20. In some embodiments, multiple latching tongues 21 and locking tongues 25 can be provided on the latching sleeve 20.

Figure 8:
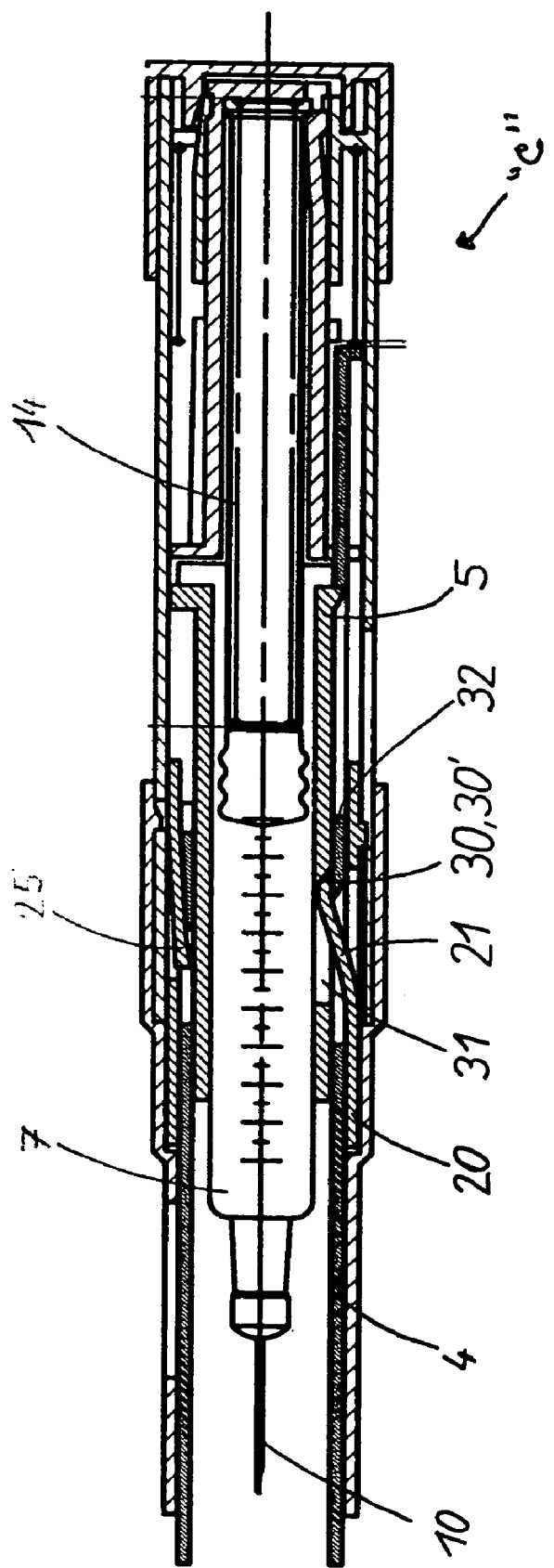
FIG. 8 depicts another embodiment of an auto-injector in accordance with the invention, in the latching position.

FIG. 8 shows a latching member in the form of a latching sleeve 20 which comprises a latching tongue 21 which comprises a surface 30 running or extending obliquely with respect to the longitudinal axis of the auto-injector, on its facing side. The tip of the oblique surface 30 abuts the outer side of the latching tongue 21. The sliding sleeve 5 comprises a cavity 31 into which the latching tongue 21 protrudes in the latching position. The edge of the cavity 31 opposite the oblique surface 30 of the latching tongue 21 comprises an oblique surface 30' which runs or extends generally parallel to the oblique surface 30 of the latching tongue 21. (In some embodiments, an oblique surface could be provided directly on the active agent container 7, such that the sliding sleeve 5 can be omitted.) The two oblique surfaces 30 and 30' come to rest on each other. The needle protecting tube 4 is at least partially arranged between the latching sleeve 20 and the sliding sleeve 5, wherein the latching tongue 21 protrudes through a cavity in the needle protecting tube 4 into the cavity 31 of the sliding sleeve 5. A part 32 of the needle protecting tube 4 overlaps the abutting point of the oblique surfaces 30 and 30', such that the latching tongue 21 is locked in the latching, latched or locked position. In FIG. 8, a locking tongue 25 is also arranged on the sliding sleeve 5, on the side opposite the latching tongue 21. The locking tongue 25 protrudes into a cavity opposite it, in the needle protecting tube 4.

FIG. 9, generally analogous to FIG. 3, shows the auto-injector in a release position in which the needle protecting tube 4 is slid into the casing "C". In this position, the part 32 of the needle protecting tube 4 has been retracted from the overlapping area of the oblique surfaces 30 and 30'. The latching tongue 21 can then be moved into the cavity 31 of the needle protecting tube 4. The movement can be caused by a bias on the elastic latching tongue 21. In some preferred embodiments, however, the latching tongue 21 is slid outwards into the cavity by the pressure exerted by the driving spring 14, which acts on the oblique surface 30.

FIG. 10, generally analogous with FIG. 5, shows the auto-injector in a position in which the active agent container 7 is advanced relative to the casing "C" and the injection needle 10 is injected into a tissue. The sliding sleeve 5 has been advanced together with the active agent container 7 in a distal direction along the latching sleeve 20, wherein the latching tongue 21 comes to rest in the cavity 31 of the needle protecting tube 4.

Figure 11:
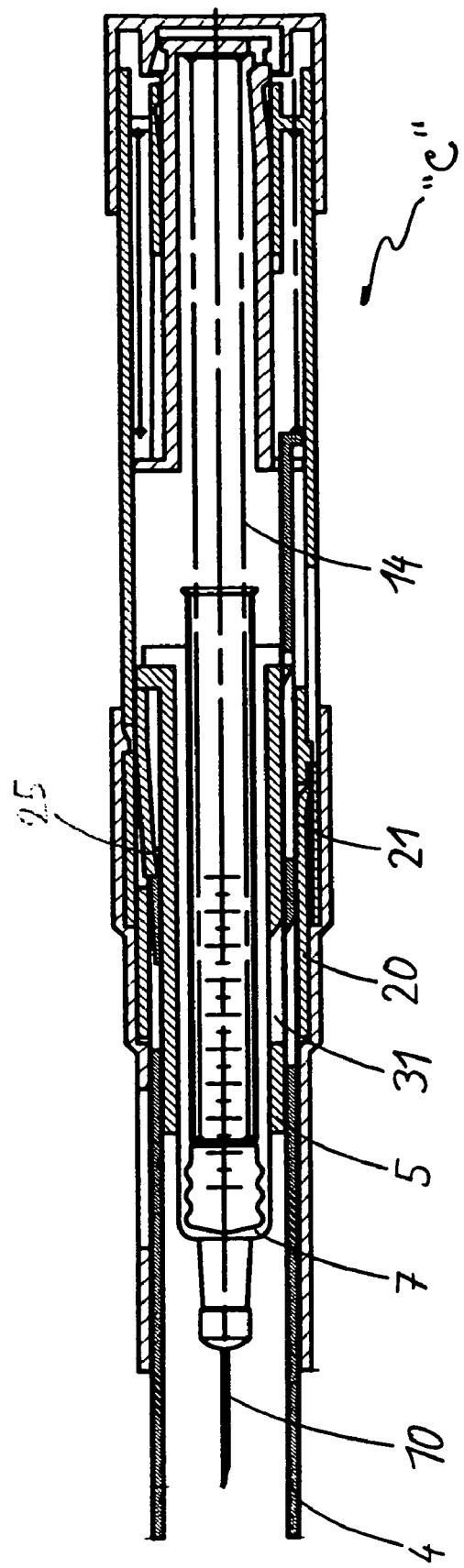
FIG. 11 depicts the auto-injector embodiment of FIG. 8 in a locking position in which the needle protecting tube is latched.

FIG. 11, generally analogous with FIG. 7, shows the auto-injector in a position in which the needle protecting tube 4 surrounds the injection needle 10 after the auto-injector has been removed from the surface of the tissue. In this embodiment, the locking tongue 25 is likewise arranged on the sliding sleeve 5. This enables a component to be omitted in the auto-injector. When the needle protecting tube 4 is advanced, the locking tongue 25 grips behind the end edge of the needle protecting tube 4, such that the needle protecting tube 4 is secured against retracting relative to the active agent container 7 or the sliding sleeve 5. When pressure is applied to the needle protecting tube 4 in the proximal direction, the needle protecting tube 4 shifted together with the sliding sleeve, the active agent container 7 and the injection needle 10, relative to the casing "C".

In the foregoing description, embodiments of the present invention, including preferred embodiments, have been presented for the purpose of illustration and description. They are not intended to be exhaustive or to limit the invention to the precise form disclosed. Obvious modifications or variations are possible in light of the above teachings. The embodiments were chosen and described to provide the best illustration of the principals of the invention and its practical application, and to enable one of ordinary skill in the art to use the invention in various embodiments and with various modifications as are suited to a particular use contemplated. All such modifications and variations are within the scope of the invention as determined by the appended claims when interpreted in accordance with the breadth they are fairly, legally, and equitably entitled.

The invention claimed is:

1. An injection device comprising:
   an elongated casing comprising a front casing part and a rear casing part;
   a container carrying an injection needle, said container axially shiftable relative to the casing;
   a piston which can be shifted in the container for the purpose of forcing out a substance therein;
   a needle protecting tube shiftable relative to the casing;
   a sliding sleeve axially shiftable and guided in the needle protecting tube accommodating the container; and
   a latching member having at least two positions, a latching position wherein the latching member prevents the container from being shifted relative to the casing, and a release position wherein the container is shiftable relative to the casing, wherein the latching member comprises at least one latching tongue arranged on a latching sleeve mounted in the casing; and wherein the latching member cannot move axially and is mounted in the front casing part; and wherein the needle protecting tube is shiftable generally into and out of the casing and wherein shifting the needle protecting tube into the casing moves the latching member form the latching position to the release position.

2. The injection device according to claim 1, wherein a locking member is provided for locking the needle protecting tube, said locking member locking the needle protecting tube in a position in which it substantially surrounds the injection needle after the injection device has been moved from a point of injection.

3. The injection device as set forth in claim 2, further comprising a needle protecting cap for being attached to the injection device, wherein when attached to the injection device, the needle protecting cap substantially encloses the injection needle prior to use and prevents the needle protecting tube from being moved into the casing.

4. An auto-injector for automatically injecting an active agent, comprising an elongated casing, wherein the casing comprises a front casing part and a rear casing part, an injection needle which can be shifted axially in the casing and connected to an active agent container, a piston which can be shifted in the active agent container for the purpose of delivering the active agent, a sliding sleeve axially shiftable and guided in a needle protecting tube accommodating the active agent container, and the needle protecting tube which can be shifted relative to the casing, wherein, in a latching position, a latching member prevents the active agent container from being shifted with respect to the casing, wherein the latching member cannot move axially and is mounted in the front casing part, and wherein that by shifting the needle protecting tube into the casing, the latching member is moved to a released position in which the active agent container is shiftable with respect to the casing.

5. The auto-injector as set forth in claim 4, wherein in the latching position the latching member is locked by the needle protecting tube.

6. The auto-injector as set forth in claim 4, wherein the latching member is formed as at least one elastically flexible latching tongue.

7. The auto-injector as set forth in claim 6, wherein the at least one latching tongue is arranged on a latching sleeve mounted in the casing.

8. The auto-injector as set forth in claim 7, wherein the at least one latching tongue is formed integrally with the latching sleeve.

9. The auto-injector as set forth in claim 6, wherein the latching tongue prevents the active agent container from being shifted with respect to the casing by abutting a flange arranged on the sliding sleeve which accommodates the active agent container, and wherein as the needle protecting tube is shifted into the casing it forces the latching tongue away from said flange.

10. The auto-injector as set forth in claim 4, wherein in the latching position, the latching member abuts a surface on the sliding sleeve which extends obliquely with respect to the longitudinal axis of the auto-injector, via a surface extending obliquely with respect to the longitudinal axis of the auto-injector.

11. The auto-injector as set forth in claim 10, wherein when the needle protecting tube is shifted into the casing, it releases the latching member and the latching member is forced out of the latching position by advancing the sliding sleeve along the oblique surfaces.

12. The auto-injector as set forth in claim 4, wherein a locking member is provided for latching the needle protecting tube and latches the needle protecting tube in a locked position in which it substantially surrounds the injection needle after the auto-injector has been lifted from a point of injection.

13. The auto-injector as set forth in claim 12, wherein, in the locked position, the needle protecting tube and the active agent container can be shifted together relative to the casing.

14. The auto-injector as set forth in claim 12, wherein the locking member is formed as at least one elastically flexible locking tongue.

15. The auto-injector as set forth in claim 14, wherein the at least one latching tongue and the at least one locking tongue are arranged on the latching sleeve and are formed integrally with the latching sleeve.

16. The auto-injector as set forth in claim 4, further comprising a needle protecting cap for substantially sealing the needle end of the auto-injector prior to use.

17. The auto-injector as set forth in claim 16, wherein the needle protecting cap substantially encloses a portion of the active agent container.

18. The auto-injector as set forth in claim 16, wherein the needle protecting cap is formed such that when attached to the auto-injector, the needle protecting cap prevents the needle protecting tube from being retracted into the casing.

19. An injection device comprising:
- a casing comprising a front casing part and a rear casing part;
- a container carrying an injection needle, said container axially shiftable relative to the casing;
- a piston which can be shifted in the container for the purpose of forcing out a substance therein;
- a needle protecting tube shiftable relative to the casing;
- a sliding sleeve axially shiftable and guided in the needle protecting tube accommodating the container;
- a locking member in the form of a locking sleeve mounted externally on the sliding sleeve; and
- at least one locking tongue protruding outwardly from the locking sleeve abutting an inner heel of the needle protecting tube, the locking tongue protruding into a cavity formed in the needle protecting tube.

20. The injection device as set forth in claim 19, further comprising:
- a needle protecting cap, wherein the needle protecting cap is removable;
- a latching sleeve that cannot move axially and is mounted in the front casing part; and
- at least one latching tongue arranged on the latching sleeve, wherein the free end of the latching tongue abuts a flange of the sliding sleeve preventing the sliding sleeve from being pulled forward together with the container when the needle protecting cap is removed.

21. An auto-injector comprising:
- a casing:
- an injection needle which can be shifted axially in the casing and connected to an active agent container, wherein the active agent container is prevented from being undersirably pulled forward;
- a piston which can be shifted in the active agent container;
- a sliding sleeve axially shiftable; and
- a latching member comprising at least one latching tongue, wherein, in a latched position, the latching member prevents the active agent container from being shifted with respect to the casing, and wherein, in a released position, the active agent container is shiftable with respect to the casing; and wherein the at least one latching tongue is arranged on a latching sleeve mounted in the casing; further comprising a needle protecting tube, wherein the at least one latching tongue prevents the active agent container from being shifted with respect to the casing by abutting a flange on the sliding sleeve which accommodates the active agent container, and wherein as the needle protecting tube is shifted into the casing it forces the latching tongue away from said flange.

22. The auto-injector as set forth in claim 21, wherein the at least one latching tongue is elastically flexible.

23. The auto-injector as set forth in claim 21, wherein the at least one latching tongue is formed integrally with the latching sleeve.

24. The auto-injector as set forth in claim 21, wherein the latching tongue is moveable relative to the casing and the latching sleeve is fixed relative to the casing.

25. The auto-injector as set forth in claim 21, further comprising a needle protecting tube.

26. The auto-injector as set forth in claim 25, wherein in the latched position, the latching member abuts a surface on the sliding sleeve which extends obliquely with respect to the longitudinal axis of the auto-injector, via a surface extending obliquely with respect to the longitudinal axis of the auto-injector.

27. The auto-injector as set forth in claim 26, wherein when the needle protecting tube is shifted into the casing, it releases the latching member and the latching member is forced out of the latched position by advancing the sliding sleeve along the oblique surfaces.

28. The auto-injector as set forth in claim 25, wherein a locking member is provided for latching the needle protecting tube and latches the needle protecting tube in a locked position in which it substantially surrounds the injection needle after the auto-injector has been lifted from a point of injection.

29. The auto-injector as set forth in claim 28, wherein, in the locked position, the needle protecting tube and the active agent container can be shifted together relative to the casing.

30. The auto-injector as set forth in claim 28, wherein the locking member is formed as at least one elastically flexible locking tongue.

31. The auto-injector as set forth in claim 30, wherein the at least one latching tongue and the at least one locking tongue are arranged on the latching sleeve and are formed integrally with the latching sleeve.

32. The auto-injector as set forth in claim 25, wherein in the latched position the latching member is locked by the needle protecting tube.

33. The auto-injector as set forth in claim 25, further comprising a needle protecting cap for substantially sealing the needle end of the auto-injector prior to use.

34. The auto-injector as set forth in claim 33, wherein the needle protecting cap substantially encloses a portion of the active agent container.

35. The auto-injector as set forth in claim 33, wherein the needle protecting cap is formed such that when attached to the auto-injector, the needle protecting cap prevents the needle protecting tube from being retracted into the casing.

36. An auto-injector comprising:
- a casing:
- an injection needle which can be shifted axially in the casing and connected to an active agent container, wherein the active agent container is prevented from being undersirably pulled forward;
- a piston which can be shifted in the active agent container;
- a needle protecting tube shiftable relative to the casing;
- a sliding sleeve axially shiftable; and
- a latching member comprising at least one latching tongue, wherein, in a latched position, the latching member prevents the active agent container from being shifted with respect to the casing, and wherein, in a released position, the active agent container is shiftable with respect to the casing,
- wherein, in the latched position, the latching member abuts a surface on the sliding sleeve which extends obliquely with respect to the longitudinal axis of the auto-injector, via a surface extending obliquely with respect to the longitudinal axis of the auto-injector, and
- wherein the at least one latching tongue prevents the active agent container from being shifted with respect to the casing by abutting a flange on the sliding sleeve which accommodates the active agent container.

37. The auto-injector as set forth in claim 36, further comprising a needle protecting tube, wherein as the needle protecting tube is shifted into the casing, it forces the latching tongue away from the flange.

* * * * *